(12) United States Patent
Munn (10) Patent No.: US 9,566,194 B2
(45) Date of Patent: Feb. 14, 2017

(54) TAMPON (71) Applicant: Eat Don't Talk, Inc., Encino, CA (US)

(72) Inventor: Lisa Olivia Munn, Encino, CA (US)

(73) Assignee: Eat Don't Talk, Inc., Encino, CA (US)

( * ) Notice: Subject to any disclaimer, the term of this patent is extended or adjusted under 35 U.S.C. 154(b) by 0 days.

(21) Appl. No.: 14/873,390

(22) Filed: Oct. 2, 2015

(65) Prior Publication Data

US 2016/0095757 A1 Apr. 7, 2016

Related U.S. Application Data

(60) Provisional application No. 62/059,301, filed on Oct. 3, 2014.

(51) Int. Cl.
*A61F 13/34* (2006.01)
*A61F 13/20* (2006.01)

(52) U.S. Cl.
CPC ........... *A61F 13/34* (2013.01); *A61F 13/2094* (2013.01)

(58) Field of Classification Search
CPC ...... A61F 13/34; A61F 6/08; A61F 13/15756; A61F 13/2082; A61F 13/208; A61F 13/204; A61K 9/0036
USPC .......................................................... 604/904
See application file for complete search history.

(56) References Cited

U.S. PATENT DOCUMENTS

| 812,770 | A | 2/1906 | Pond |
|---|---|---|---|
| 3,863,636 | A | 2/1975 | Johnson |
| 4,351,338 | A | 9/1982 | Langlois et al. |
| 5,074,855 | A | 12/1991 | Rosenbluth et al. |
| 5,370,633 | A * | 12/1994 | Villalta ............... A61F 13/2051 128/830 |
| 5,988,386 | A * | 11/1999 | Morrow .................. A61F 13/26 206/440 |
| 6,599,279 | B2 | 7/2003 | Taylor |
| 6,676,625 | B2 | 1/2004 | Bernard |
| 6,687,911 | B2 | 2/2004 | Fitz |
| 8,568,381 | B2 | 10/2013 | Mueller et al. |
| 2002/0068918 | A1 | 6/2002 | Durel-Crain |
| 2003/0131455 | A1 | 7/2003 | Rajala |
| 2003/0153864 | A1 | 8/2003 | Chaffringeon |
| 2003/0181844 | A1 | 9/2003 | Bernard |
| 2004/0254557 | A1 | 12/2004 | Kraemer |
| 2007/0073257 | A1* | 3/2007 | Buck ................... A61F 13/2051 604/385.18 |
| 2007/0191805 | A1 | 8/2007 | Kramer |

(Continued)

FOREIGN PATENT DOCUMENTS

| DK | WO 9956678 A1 * | 11/1999 | ............ A61F 13/34 |
|---|---|---|---|
| JP | 3133451 A | 6/1991 | |

(Continued)

*Primary Examiner* — Peter S Vasat
(74) *Attorney, Agent, or Firm* — Tomlinson Rust McKinstry Grable (57) ABSTRACT

A tampon for use in feminine hygiene. The tampon has an elongate body and a string. The elongate body has a first end, a second end, and an interior. The string has a first end, a second end, and an intermediate portion. The first end and the second end of the string are attached to the interior of the elongate body such that the first end and the second end are separated and the intermediate portion of the string forms a loop that extends from the second. end of the elongate body. The loop provides a grip to assist in removing the tampon.

24 Claims, 5 Drawing Sheets

(56) References Cited

U.S. PATENT DOCUMENTS

| | | | |
|---|---|---|---|
| 2008/0033337 A1* | 2/2008 | Dougherty, Jr. | ........ A61F 13/26 604/15 |
| 2008/0097366 A1* | 4/2008 | Mathews | ............ A61F 13/2068 604/385.18 |
| 2008/0234650 A1 | 9/2008 | Smith | |
| 2008/0287902 A1 | 11/2008 | Edgett et al. | |
| 2011/0009803 A1 | 1/2011 | Dougherty | |
| 2011/0092940 A1 | 4/2011 | Fung | |
| 2011/0152742 A1 | 6/2011 | Winkel | |
| 2013/0231626 A1 | 9/2013 | Riordan | |

FOREIGN PATENT DOCUMENTS

| | | |
|---|---|---|
| JP | 2006271919 A | 10/2006 |
| WO | 9908560 A1 | 2/1999 |

* cited by examiner

TAMPON

CROSS REFERENCE TO RELATED APPLICATION

This application claims the benefit of provisional patent application Ser. No. 62/059,301 filed on Oct. 3, 2014, the entire contents of which are incorporated herein by reference.

FIELD

This invention relates generally to tampons for use in feminine hygiene, in particular, tampons with a string in the form of a loop.

SUMMARY

The present invention is directed to a tampon comprising an elongate body and a string. The elongate body comprises a first end, a second end, and an interior. The string comprises a first end, a second end, and an intermediate portion. The first end and the second end of the string are attached to the interior of the elongate body such that the first end and the second end of the string are separated or spaced apart from one another. The intermediate portion of the string forms a loop that extends from the second end of the elongate body. The elongate body is folded to enclose the first end and the second end of the string within the interior of the elongate body.

The present invention is also directed to a method of manufacturing a tampon. The method comprises the steps of providing an elongate body comprising a first end, a second end, and an interior and providing a string comprising a first end, a second end, and an intermediate portion. The method further comprises the steps of attaching the first end and the second end of the string to the interior of the elongate body such that the first end and the second end of the string are spaced apart from one another and the intermediate portion of the string extends from the second end of the elongate body and forms a loop, and folding the elongate body to enclose the first end and the second end of the string within the interior of the elongate body.

DETAILED DESCRIPTION

Females commonly wear tampons during their menstrual periods to absorb the flow. The tampon commonly used is a super absorbent pad of cotton, rayon, or other material that is rolled or folded into itself to make a generally oblong object fit for being inserted into the vaginal canal. The vaginal wall holds the tampon in place until removed. Most tampons provide a straight string which extends from the vaginal opening and labia while the tampon is in place inside the vagina. The string provides a mechanism to remove the tampon when needed. The length and straight nature of the string may be a problem for tampon users. The string may be difficult to grip and pull during tampon removal. Thus, the string has to be fairly long to allow the fingers to get a solid grip on the string before pulling to remove the tampon. Because it is so long, the string often hangs out of bathing suits or underwear or may get in the way of the urine stream. Therefore, there remains a need for improved tampons.

Figure 1:
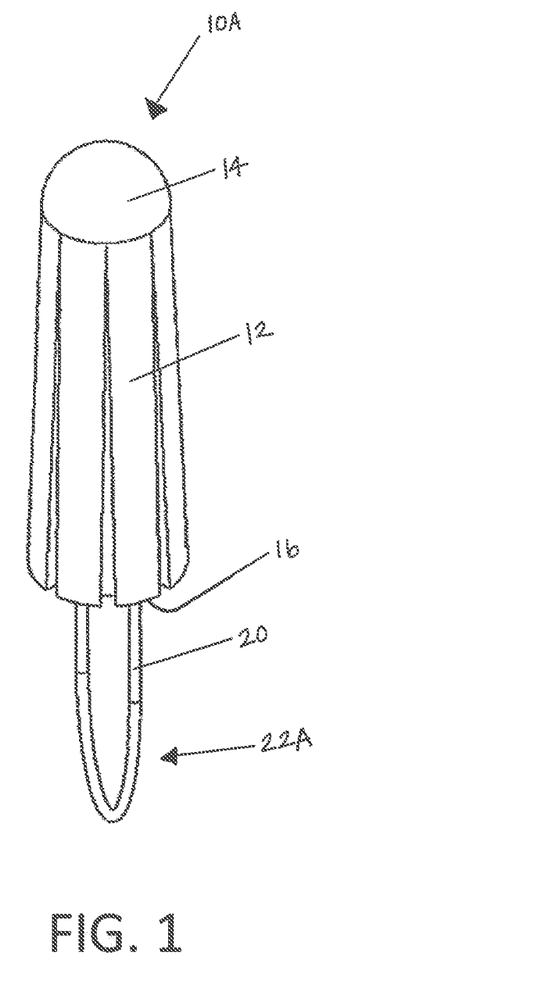
FIG. 1 is a top perspective view of the tampon of the present invention.
Figure 2:
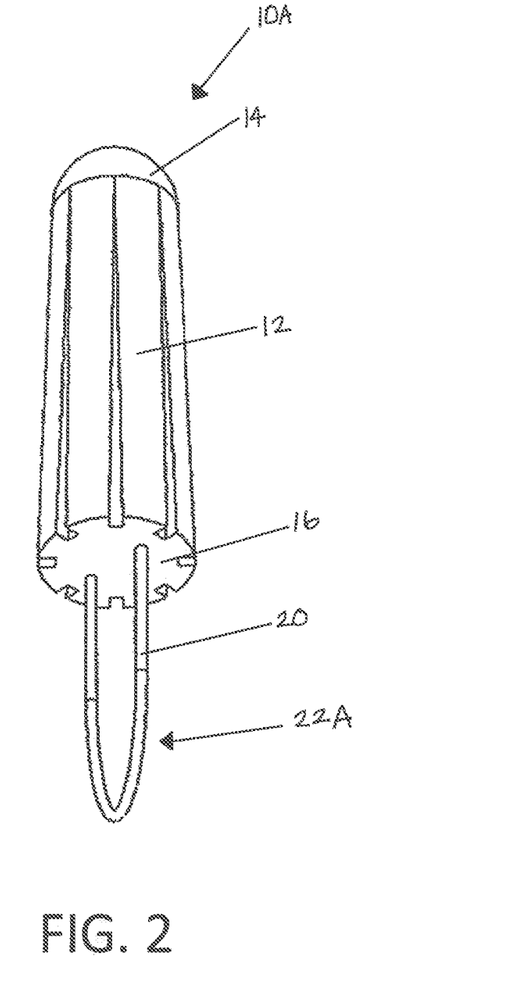
FIG. 2 is a bottom perspective view of the tampon of FIG. 1.
Figure 3:
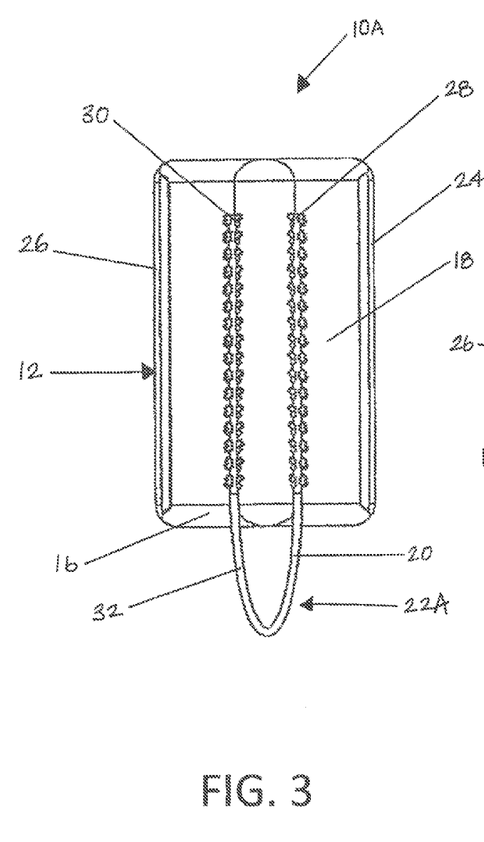
FIG. 3 is a front view of the interior of the tampon of FIG. 1.

Turning now to FIGS. 1 and 2, a tampon 10A of the present invention is shown. The tampon 10A comprises an elongate body 12 that may be rolled or folded together to form a generally oblong shape. The elongate body 12 comprises a first end 14, a second end 16, and an interior 18 (FIG. 3). The tampon further comprises a string 20. The string 20 extends from the second end 16 of the elongate body 12 such that it forms a loop 22A.

Figure 4:
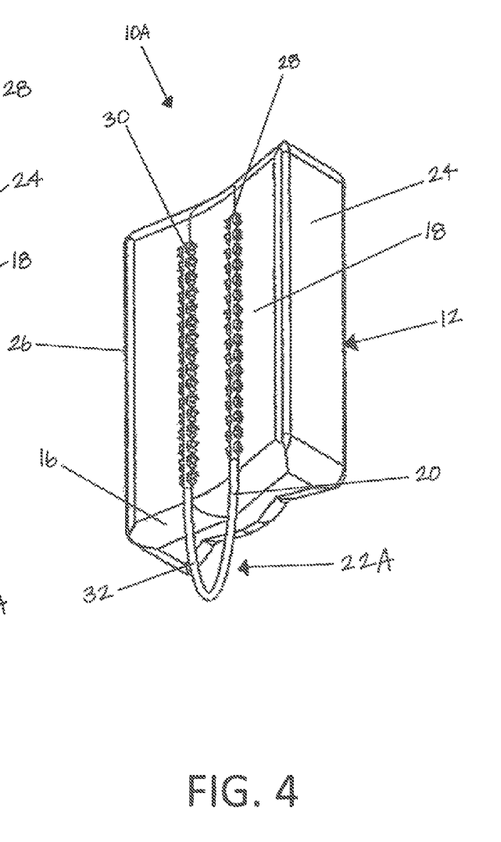
FIG. 4 is a bottom perspective view of the interior of the tampon of FIG. 1.

Referring now to FIGS. 3 and 4, the tampon 10A is shown unrolled to expose the interior 18 of the elongate body 12. The elongate body 12 comprises a first side 24 and a second side 26 that are visible when the tampon 10A is unrolled or unfolded. The string 20 in FIGS. 3 and 4 is shown attached to a central portion of the interior 18 of the elongate body 12. The central portion of the interior 18 of the elongate body 12 is a portion of the interior that is away from the periphery of the elongate body or away from the first side 24 and the second 26. The string 20 comprises a first end 28, a second end 30, and an intermediate portion 32. The first end 28 and the second end 30 of the string 20 are attached to the central portion of the interior 18 of the elongate body 12 such that they are separated or spaced apart from one another. The string 20 may be sewn, glued, or attached to the interior 18 of the elongate body 12 by any method known in the art to ensure the string remains securely attached to the tampon 10A. The intermediate portion 32 of the string 20 extends from the second end 16 of the tampon 10A and forms the loop 22A.

Continuing with FIGS. 3 and 4, the loop 22A may extend any distance from the second end 16 of the tampon 10A as desired. For example, the loop 22A may extend greater than one inch or less than one inch from the second end 16 of the tampon 10A. Preferably, the loop 22A will extend far enough from the second end 16 of the elongate body 12 to cross the vaginal wall and reach the outside of the vaginal opening, such that it rests inside the wearer's garment. The loop 22A avoids problems encountered with long strings typically used with tampons because the loop is preferably short enough that it will not accidently be exposed from a garment and stay out of the way of the urine stream. The loop 22A also provides increased tensile strength to allow for a better grip when removing the tampon 10A from the vaginal canal. The loop 22A may be of a size sufficient for receiving one or two fingers to effectively grip the loop. The string 20 may be made of a reinforced material like those currently used in the art. The string 20 may also comprise other materials known in the art suitable for use with the tampon 10A.

Referring now to FIGS. 1-4, the tampon 10A may be manufactured by attaching the first end 28 and the second end 30 of the string 20 to the interior 18 of the elongate body 12. The first end 28 and the second end 30 may be attached such that they are spaced apart or separated from one another, as shown in FIGS. 3 and 4. The elongate body 12 may then be folded or rolled together such that the first side 24 and the second side 26 of the elongate body 12 are attached to one another. The first side 24 and the second side 26 may be sewn or glued together or attached together by other means known in the art to ensure the tampon 10A remains folded. Attaching the first side 24 and the second side 26 of the elongate body 12 to one another encloses the first end 28 and the second end 30 of the string 20 within the interior 18 of the elongate body. The first end 28 and the second end 30 of the string 20 are enclosed within the interior 18 of the elongate body 12 such that they remain separated or spaced apart from one another. This can be seen by looking at the second end 16 of the elongate body 12 in FIG. 2. In the tampon 10A shown in FIGS. 1-4, the first end 28 and the second end 30 of the string 20 remain spaced apart and never touch or join together.

Figure 5:
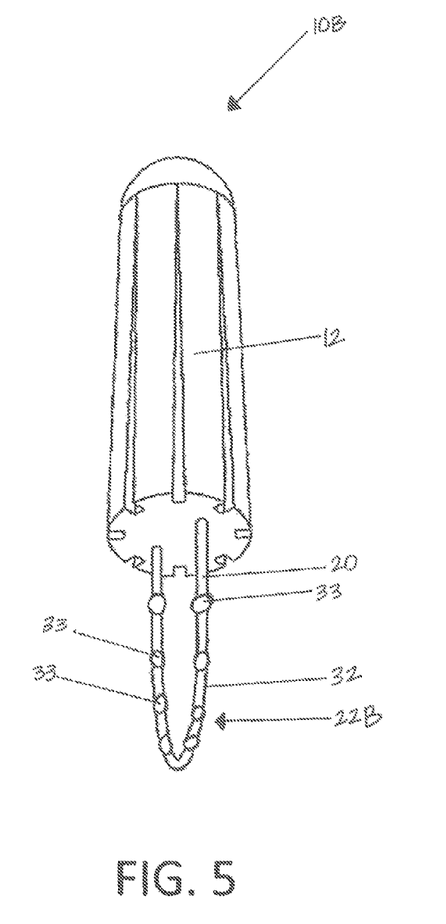
FIG. 5 is a bottom perspective view of an alternative embodiment of the tampon of FIG. 1.
Figure 6:
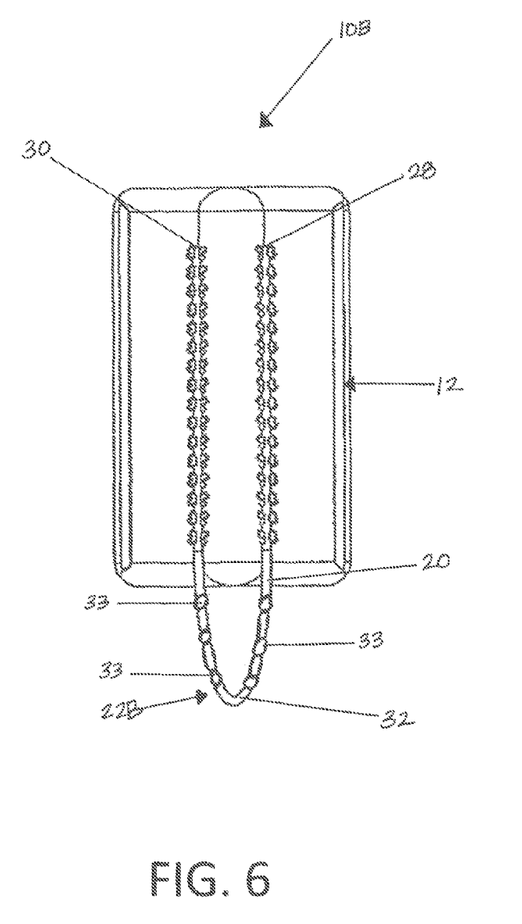
FIG. 6 is a front view of the interior of the alternative embodiment shown in FIG. 5.

Turning now to FIGS. 5 and 6, an alternative embodiment of the tampon 10B is shown. The tampon 10B is identical to tampon 10A (FIGS. 1-4) except that the intermediate portion 32 or loop 22B of the string 20 comprises a series of knots 33. The series of knots 33 provide additional grip for the user when removing the tampon 10B. The series of knots 33 also provide more surface area for the string 20 to help locate the string prior to tampon removal. The series of knots 33 may be formed in the intermediate portion 32 of the string 20 prior to attaching the first end 28 and the second end 30 of the string to the elongate body 12. Alternatively, a series of small beads rather than a series of knots 33 may be placed along the intermediate portion 32 of the string 20 to assist in tampon removal. The string 20 may also comprise other gripping means known in the art if desired.

Figure 7:
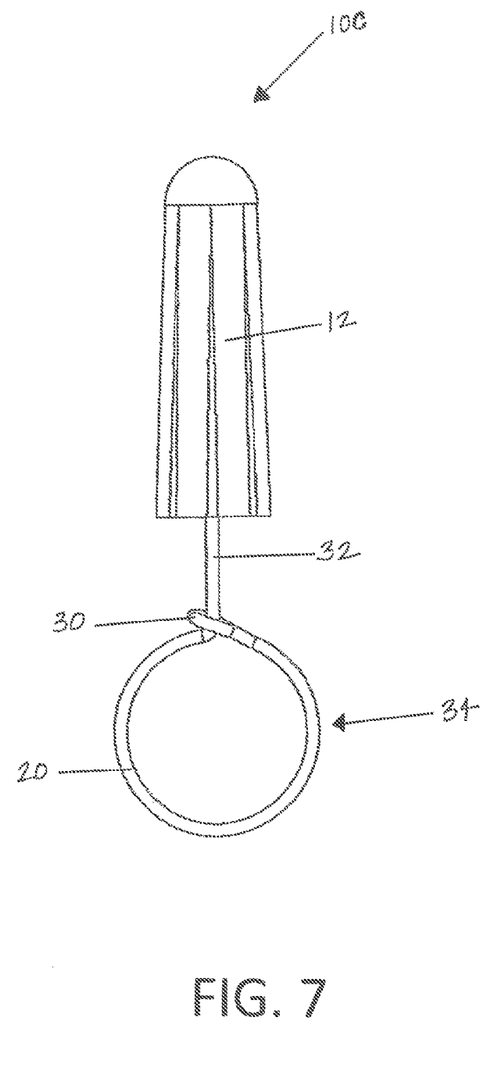
FIG. 7 is a front view of a second alternative embodiment of the tampon of FIG. 1.

Referring now to FIG. 7, a second alternative embodiment of the tampon IOC is shown. In FIG. 7, only the first end (not shown) of the string 20 is attached to the interior of the elongate body 12. The second end 30 of the string 20 is attached to the intermediate portion 32 of the string such that the string forms a loop 34. The intermediate portion 32 of the string 20 shown in FIG. 7 may also comprise a series of knots 33 (FIGS. 5-6) or other added gripping means if desired to assist in tampon removal.

Figure 8:
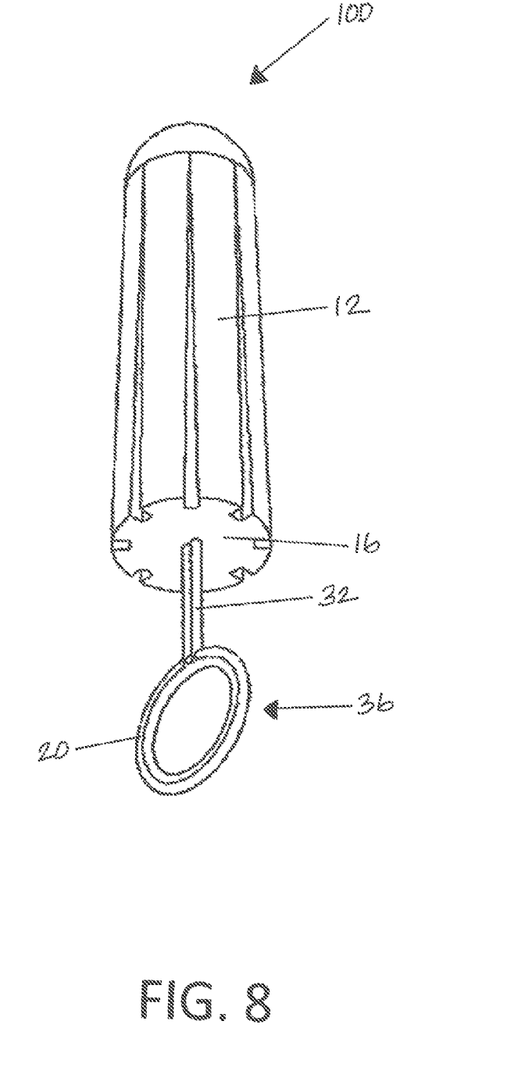
FIG. 8 is a bottom perspective view of a third alternative embodiment of the tampon of FIG. 1.
Figure 9:
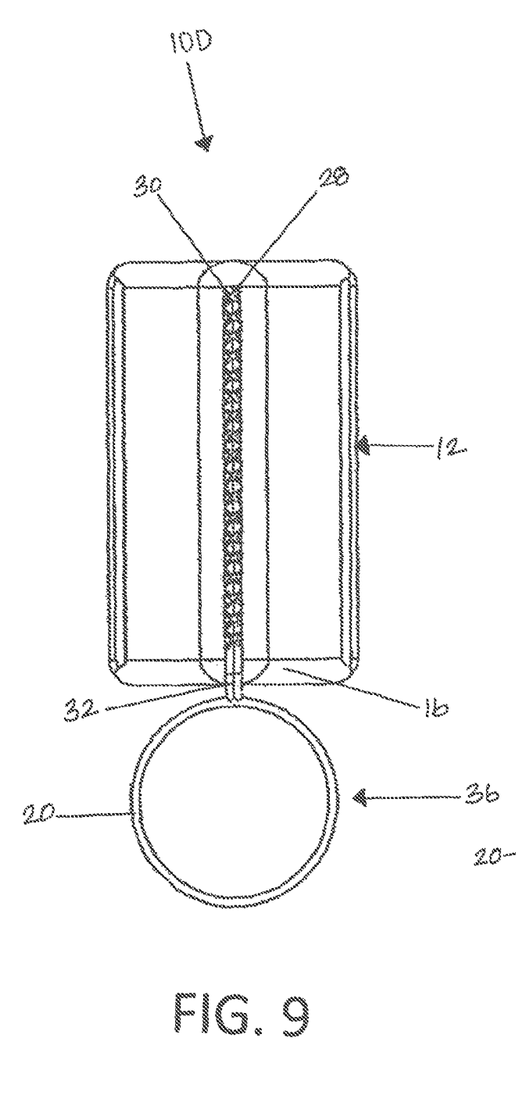
FIG. 9 is a front view of the interior of the tampon of FIG. 8.
Figure 10:
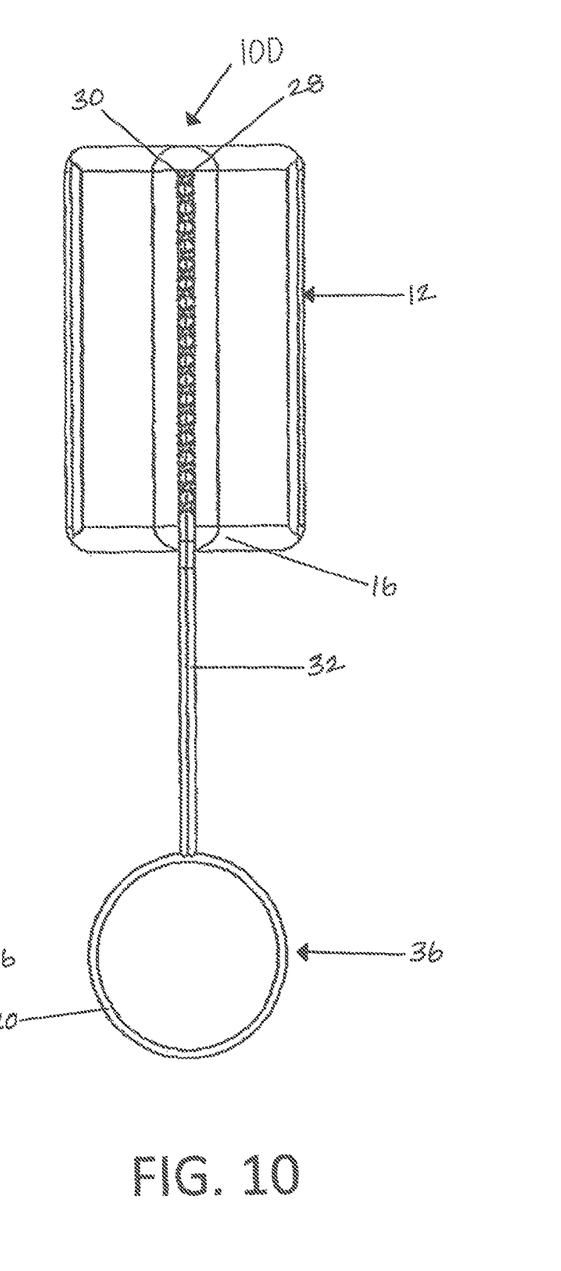
FIG. 10 is a front view of the interior of an alternative embodiment of the tampon of FIG. 8.

A third alternative embodiment of the tampon 10D is shown in FIGS. 8-10. In FIGS. 8-10, the first end 28 and the second end 30 of the string 20 are attached to the interior 18 of the elongate body 12. However, the first end 28 and the second end 30 are not spaced apart from one another and are instead joined together or touching, as shown in FIGS. 8-10. The first end 28 and the second end 30 of the string 20 stay touching as the intermediate portion 32 of the string extends from the second end 16 of the elongate body 12. The intermediate portion 32 is then looped so as to form a loop 36, as shown in FIGS. 8-10. The intermediate portion 32 may extend a short distance from the second end 16 of the elongate body 12 as shown in FIG. 9, or may extend a much longer distance from the elongate body before forming the loop 36, as shown in FIG. 10. The intermediate portion 32 of the string 20 shown in FIGS. 8-10 may also comprise a series of knots 33 (FIGS. 5-6) or other added gripping means if desired to assist in tampon removal.

In operation, the tampon 10A, 10B, 10C, or 10D may be used with any applicators (not shown) known in the art to assist in inserting the tampon into a vagina. The first end 14 of the tampon 10A, 10B, 10C, or 10D is inserted first into the vagina allowing the second end 16 of the tampon to be closest the vaginal opening. To remove the tampon 10A, 10B, 10C, or 10D the loop 22A, 22B, 34, or 36 may be gripped by the fingers allowing the tampon to be pulled from the vagina and discarded. The elongate body 12 is made from an absorbent material typically used in the art for making tampons, such as cotton or rayon. The absorbent material may be hydrophilic, affinity to absorb fluids, on the first end 14 of the elongate body 12 and hydrophobic, resistant to water or fluid absorption, on the second end 16 of the elongate body 12. The string 20 may be formed of or be treated with a hydrophobic or waterproof material. In this manner, the tampon 10A, 10B, 10C, or 10D will absorb fluids within the vagina and prevent fluids from entering the tampon from outside of the vagina, such as water from a swimming pool.

Various modifications can be made in the design and operation of the present invention without departing from its spirit. Thus, while the preferred construction and modes of operation of the invention have been explained in what is now considered to represent its best embodiments, it should be understood that within the scope of the appended claims, the invention may be practiced otherwise than as specifically illustrated and described.

What is claimed is:

1. A tampon comprising:
   an elongate body comprising a first end, a second end, and an interior;
   a string comprising a first end, a second end, and an intermediate portion;
   wherein the first end and the second end of the string are independently of one another attached to a central portion of the interior of the elongate body such that the first end and the second end of the string are separated and remain spaced apart and never touch or join together;
   wherein the intermediate portion of the string forms a loop extending from the second end of the elongate body; and
   wherein the elongate body is folded to form a substantially solid generally cylindrical shape to enclose the first end and the second end of the string within the interior of the elongate body.

2. The tampon of claim 1 wherein a portion of the elongate body comprises an absorbent material.

3. The tampon of claim 1 wherein the first end and the second end of the string are sewn to the interior of the elongate body.

4. The tampon of claim 1 wherein the first end and the second end of the string are glued to the interior of the elongate body.

5. The tampon of claim 1 wherein a portion of the loop that extends from the second end of the elongate body is less than one inch.

6. The tampon of claim 1 wherein a portion of the loop that extends from the second end of the elongate body is greater than one inch.

7. The tampon of claim 1 wherein the string comprises a reinforced material.

8. The tampon of claim 1 wherein a portion of the tampon comprises a waterproof material.

9. The tampon of claim 1 wherein the intermediate portion of the string comprises a series of knots.

10. A tampon comprising:
    an elongate body comprising a first end, a second end, an interior, a first side and a second side;

a string comprising a first end, a second end, and an intermediate portion;

wherein the first end and the second end of the string are independently of one another attached to a central portion of the interior of the elongate body such that the first end and the second end of the string are spaced apart from one another and remain spaced apart and never touch or join together;

wherein the intermediate portion of the string forms a loop extending from the second end of the elongate body; and wherein the elongate body is folded and the first side is attached to the second side to form a substantially solid generally cylindrical shape to enclose the first end and the second end of the string within the interior of the elongate body.

11. The tampon of claim 10 wherein a portion of the elongate body comprises an absorbent material.

12. The tampon of claim 10 wherein the first end and the second end of the string are sewn to the interior of the elongate body.

13. The tampon of claim 10 wherein the first end and the second end of the string are glued to the interior of the elongate body.

14. The tampon of claim 10 wherein the loop extends from the second end of the elongate body proximate a central longitudinal axis of the elongate body.

15. The tampon of claim 10 wherein a portion of the loop that extends from the second end of the elongate body is greater than one inch.

16. The tampon of claim 10 wherein a portion of the tampon comprises waterproof material.

17. The tampon of claim 10 wherein the intermediate portion of the string comprises a series of knots.

18. A method of manufacturing a tampon comprising the steps of:

providing an elongate body comprising a first end, a second end, and an interior;

providing a string comprising a first end, a second end, and an intermediate portion;

attaching the first end and the second end of the string independently of one another to a central portion of the interior of the elongate body such that the first end and the second end of the string are spaced apart from one another and remain spaced apart and never touch or join together, and the intermediate portion of the string extends from the second end of the elongate body and forms a loop; and folding the elongate body to form a substantially solid generally cylindrical shape to enclose the first end and the second end of the string within the interior of the elongate body.

19. The method of claim 18 further comprising the step of forming the elongate body from an absorbent material.

20. The method of claim 18 further comprising the step of sewing the first end and the second end of the string to the interior of the elongate body.

21. The method of claim 18 further comprising the step of gluing the first end and the second end of the string to the interior of the elongate body.

22. The method of claim 18 further comprising the step of forming a portion of the tampon from a waterproof material.

23. The method of claim 18 further comprising the step of extending the loop greater than one inch from the second end of the elongate body.

24. The method of claim 18 further comprising the step of forming a series of knots in the intermediate portion of the string.

* * * * *

UNITED STATES PATENT AND TRADEMARK OFFICE
CERTIFICATE OF CORRECTION

| | | |
|---|---|---|
| PATENT NO. | : 9,566,194 B2 | Page 1 of 1 |
| APPLICATION NO. | : 14/873390 | |
| DATED | : February 14, 2017 | |
| INVENTOR(S) | : Munn | |

It is certified that error appears in the above-identified patent and that said Letters Patent is hereby corrected as shown below:

On the Title Page

Item [57], Line 8, please delete "second." and substitute therefore --second--.

In the Specification

Column 3, Line 39, delete "IOC" and substitute therefore --10C--.

Signed and Sealed this
Twenty-eighth Day of March, 2017

Michelle K. Lee
*Director of the United States Patent and Trademark Office*